United States Patent [19]
Kitchen et al.

[11] Patent Number: 5,344,781
[45] Date of Patent: Sep. 6, 1994

[54] DETECTION AND PREVENTION OF HYDROCARBON LEAKAGE FROM UNDERGROUND STORAGE TANKS

[75] Inventors: Nancy E. Kitchen, Rio Rancho, N. Mex.; Edward F. Kitchen, Neshanic Station, N.J.; George H. Kitchen, III, Rio Rancho, N. Mex.

[73] Assignee: International Lubrication and Fuel Consultants, Albuquerque, N. Mex.

[21] Appl. No.: 687,460

[22] Filed: Apr. 17, 1991

[51] Int. Cl.$^5$ .............................. G01N 33/24
[52] U.S. Cl. ...................... 436/29; 422/101; 422/102; 436/30; 436/31; 436/60
[58] Field of Search ............ 436/28, 29, 30, 27, 436/39, 31, 60; 422/101, 102, 61, 104; 435/9

[56] References Cited

U.S. PATENT DOCUMENTS

| | | | |
|---|---|---|---|
| 2,269,889 | 1/1942 | Blau | 23/230 |
| 2,292,300 | 8/1942 | Smith et al. | 23/230 |
| 2,367,664 | 1/1945 | Campbell | 436/30 |
| 2,431,487 | 11/1947 | Larsen | 436/30 |
| 2,478,478 | 8/1949 | Grebe | 204/197 |
| 2,539,082 | 1/1951 | Hustinx | 422/101 |
| 2,733,135 | 1/1956 | Huckabay | 436/31 |
| 2,839,722 | 6/1958 | Marsh | 324/30 |
| 3,168,455 | 2/1965 | Shapiro et al. | 204/147 |
| 3,254,959 | 6/1966 | Fallgatter | 436/31 |
| 3,407,042 | 10/1968 | Slentz | 436/30 |
| 4,201,549 | 5/1980 | Tepe et al. | 422/102 |
| 4,775,513 | 10/1988 | Marks | 422/61 |
| 5,028,543 | 7/1991 | Finch et al. | 436/60 |

FOREIGN PATENT DOCUMENTS 2069693  8/1981  United Kingdom ............... 422/61

OTHER PUBLICATIONS

Baxter Catalog; 1991–92; "Dishes", pp. 763–765.
Nelson et al; "Correlated Organic Laboratory Experiences"; 1973; 102–104.

*Primary Examiner*—Robert J. Warden
*Assistant Examiner*—Krisanne M. Thornton
*Attorney, Agent, or Firm*—Deborah A. Peacock; Rod D. Baker; Jeffrey D. Myers

[57] ABSTRACT

Methods and apparatuses for detecting leakage of hydrocarbons from and preventing corrosion of underground storage tanks. Soil samples near an underground storage tank are taken and analyzed in the field, preferably using hexane as a solvent to detect the presence of hydrocarbons such as heating and waste oil. The soil-to-tank potential of the tank and the presence of water within the tank are measured and, if warranted, cathodic protection provided to the tank to prevent corrosion or further corrosion.

9 Claims, 3 Drawing Sheets

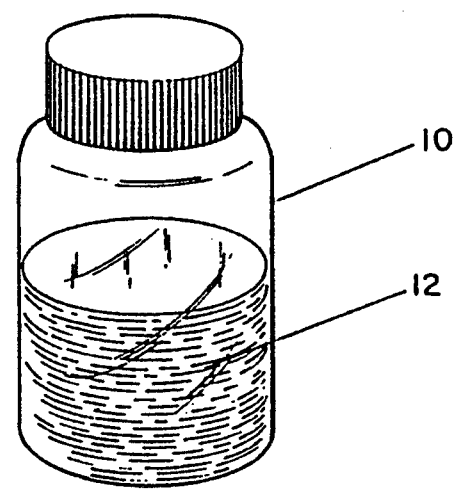
FIG—1a
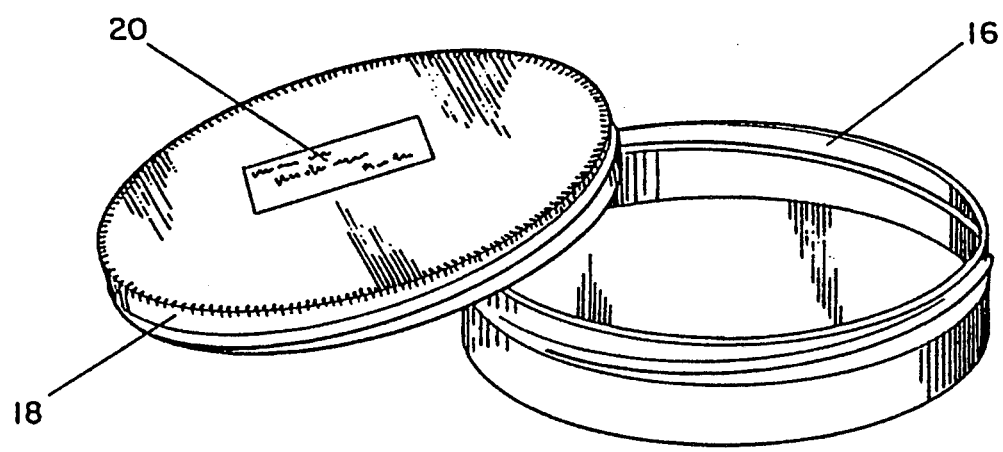
FIG—1b
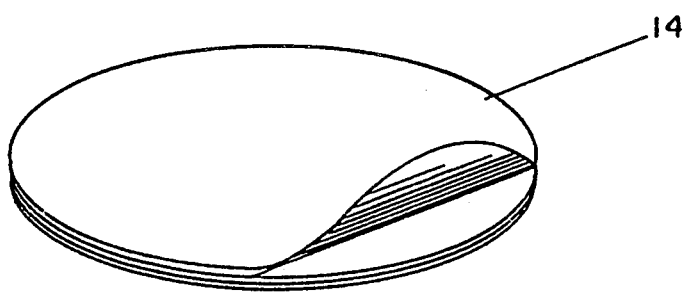
FIG—1c

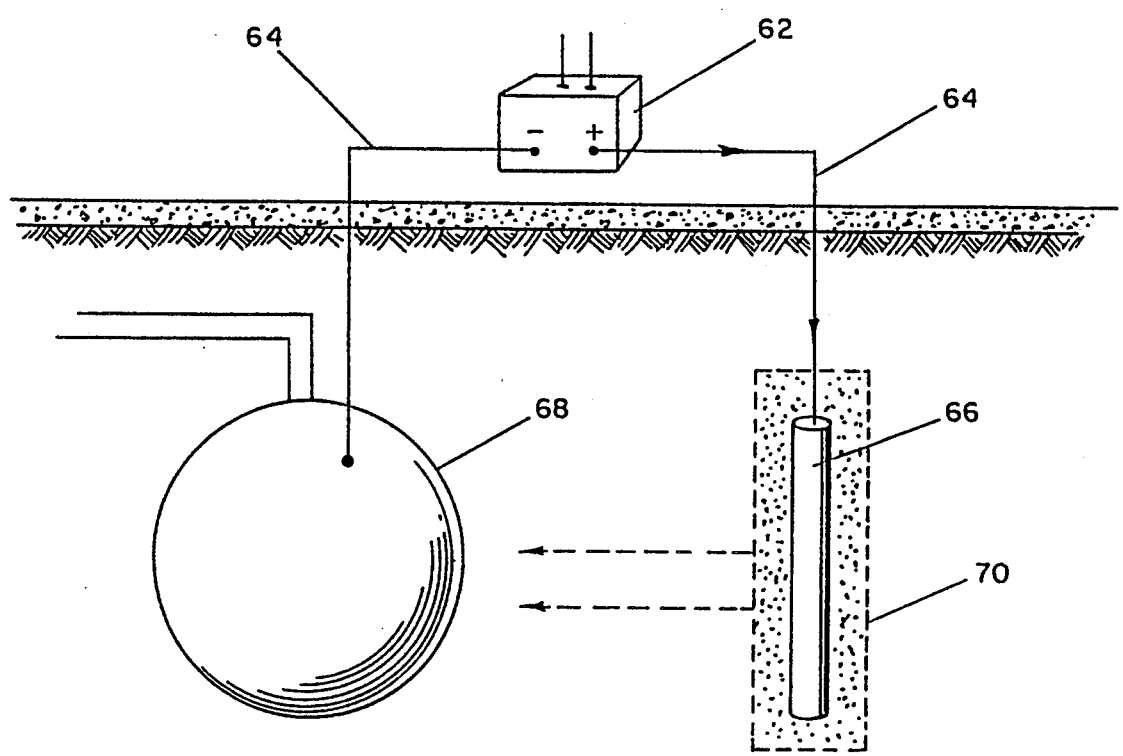
FIG—4

DETECTION AND PREVENTION OF HYDROCARBON LEAKAGE FROM UNDERGROUND STORAGE TANKS

BACKGROUND OF THE INVENTION

1. Field of the Invention (Technical Field)

The invention described and claimed herein relates generally to a method and apparatus for detecting leakage of hydrocarbons from and preventing corrosion of underground storage tanks. More particularly, the present invention relates to field methods and apparatuses for analyzing soil samples taken near an underground storage tank for the presence of hydrocarbons, for measuring the soil-to-tank potential of a tank, for detection of water in a tank, and for protecting a tank from corrosion by supplying current flow through the metal of the tank.

2. Background Art

Thousands of underground tanks storing petroleum products are located throughout the world. With each, a potential for leakage of the stored products exists, and for metal underground storage tanks, a potential for corrosion. Even though an underground storage tank may have a long-term protective coating (e.g., 30-year coating), the tank could get scratched or punctured, particularly during installation, which necessitates periodic testing for leakage.

The area around an underground storage tank must be inspected periodically to determine whether hydrocarbon leakage has occurred. The inspection process heretofore has involved taking soil samples and sending them to a laboratory for inspection. The present invention permits an on-site determination of whether a soil sample is contaminated by hydrocarbons. A laboratory need only be involved to determine the type, amount and possible source of any hydrocarbons detected.

In the prior art, soil samples are collected in the field and then sent to a laboratory for field testing. It is not known in the art to detect the presence of hydrocarbons, using an on-site field kit, with an extraction solvent.

Previously known devices exist in the art which provide for field prospecting for oil deposits by analysis of soil samples. U.S. Pat. No. 2,269,889, to Blau, entitled *Process for Locating Valuable Subterranean Deposits*, describes a device for locating subterranean deposits of hydrocarbons by field analysis of surface soil samples. The device detects the presence of certain byproducts of hydrocarbon consuming bacteria. A soil sample is combined with water and sodium peroxide, which produces a characteristic color change in the sample if the bacterial byproducts are present. U.S. Pat. No. 2,292,300, to Smith, entitled *Photochemical Exploration Method*, describes a device for prospecting for hidden petroleum deposits by laboratory analysis of the alkaline salt content of surface soil samples. Soil samples are combined with water and silver nitrate, and the tint of the resulting solution indicates the concentration of alkaline salts within the soil. Anomalies in concentrations may indicate a hydrocarbon deposit below the point or points at which the anomalous sample or samples were taken. These patents do not disclose field testing of soil surrounding underground storage tanks, nor the use of hexane in a soil sample test.

In the laboratory, testing of soil samples generally involves the use of a chlorofluorocarbon extraction solvent which is known to cause environmental problems in its depletion of the ozone layer. It is a purpose of the present invention to use solvents, such as hexane, not known to cause ozone depletion or other environmental problems.

Metal underground storage tanks should also be tested periodically to determine how corroded they are presently, as well as their potential for further corrosion. U.S. Pat. No. 2,839,722, to Marsh, entitled *Method and Apparatus for Detecting Stray Current Corrosion*, discloses a device for detecting stray voltage in the area of an underground storage tank which may cause the tank to corrode more rapidly. It does not disclose a method or apparatus for measuring what is generally known in the art as "soil-to-tank potential."

Underground storage tanks having a non-minimal potential for corrosion should be protected by inducing current flow through them. This type of protection is generally known in the art as "cathodic protection." U.S. Pat. No. 2,478,478, to Grebe, entitled *Potential Gradient Anode for Galvanic Protection*, and U.S. Pat. No. 3,168,455, to Shapiro, et al., entitled *Corrosion Protection*, are examples of methods and devices to reduce the cost of cathodic protection.

SUMMARY OF THE INVENTION (DISCLOSURE OF THE INVENTION)

The present invention comprises a kit and method for on-site or field analysis of soil for detecting the presence of hydrocarbons. The invention comprises using a field container comprising extraction solvent reactable with hydrocarbons in an amount sufficient to mix with a soil sample, filtering solids from the mixture of the soil sample and the extraction fluid, and detecting hydrocarbon presence from inspection of the filtered extraction solvent.

In the preferred embodiment, the extraction solvent comprises hexane, the field container comprises a sealable bottle for allowing mixing by shaking of the extraction solvent and the soil sample, the filtering comprises using filter paper of 20 micron or finer porosity, and the detecting of hydrocarbons comprises evaporating the extraction fluid and inspecting any residue from evaporation (such as an evaporating dish with a cover for storage of the residue and a label for providing information). The step of detecting the presence of hydrocarbons may comprise smelling an oily smell and/or the further steps of evaporating the extraction solvent to produce a residue containing hydrocarbons, if present in the soil sample, visually detecting a colored residue, and/or feeling an oily presence in the residue. In the preferred embodiment, the method further comprises the step of drilling at least one hole from which to extract the soil at a selected location relative to an underground storage tank down to a point near the bottom of the underground storage tank.

The present invention also comprises a method for on-site analysis of the potential of a metal underground storage tank for corrosion or further corrosion. The method comprises the steps of field testing soil surrounding the underground storage tank in accordance with the method above described, providing an electrode to the soil at a predetermined location relative to the underground storage tank, measuring the voltage, providing a conductive pathway between the underground storage tank and the voltage measuring device, providing a conductive pathway between the electrode and the voltage measuring device, taking a reading from the voltage measuring device, and determining the potential of the underground storage tank to corrode or further corrode if the voltage reading is less than or greater than a predetermined soil-to-tank potential voltage. The predetermined soil-to-tank potential voltage is approximately −0.29 volts, at which voltage corrosion protection is indicated for the underground storage tank for which voltage reading greater than −0.28 volts are obtained.

The invention further comprises a method for on-site detection of water within an underground storage tank. The method comprises the steps of field testing soil surrounding the underground storage tank in accordance with the method above described, inserting a dipstick coated with a reagent reactable with water into the underground tank to detect the presence of water in the underground storage tank, removing the dipstick from the underground storage tank and visually inspecting the reagent coating on the dipstick to see if a reaction has occurred, thereby indicating the presence of water in the underground storage tank.

The present invention also comprises a method for protecting a metal underground storage tank from corrosion utilizing cathodic protection. The method comprises the steps of field testing soil surrounding the underground storage tank in accordance with the method above described, providing metal or metal alloy anode to the underground storage tank in the soil at a predetermined location relative to the underground storage tank, the underground storage tank being cathodic relative to the anode, and providing a conductive pathway between the underground storage tank and the anode. In the preferred embodiment, the anode comprises a sacrificial anode. The method of the invention may further comprise the steps of providing a conductive pathway between the anode and current generating device and providing a conductive pathway between the underground storage tank and the current generating device.

It is a primary object of the present invention to provide an easy and inexpensive field test for the on-site testing of soil surrounding an underground storage tank for contamination of the soil with hydrocarbons.

It is another object of the present invention to continue this field test with other apparatuses/methods for the detection and prevention of corrosion of metal underground storage tanks.

A primary advantage of the present invention is that test results are obtained easily and immediately, so that quick decisions can be made whether or not to repair or replace an underground storage tank or to provide corrosion protection to the existing underground storage tank.

Another advantage of the present invention is that the preferred extraction solvent used for extracting hydrocarbons from contaminated soil does not deplete the ozone layer, as is the case with chlorofluorocarbons.

An additional advantage of the present invention is that the soil testing kit may be used to judge the efficiency of cleanup efforts after a hydrocarbon spill.

This invention is particularly useful for homeowners with home heating oil tanks, by utilizing an easy and inexpensive apparatus/kit and method to test surrounding soil and prevent corrosion of underground storage tanks.

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention.

FIGS. 1a–1c are a perspective view of the leakage detection components of the field analysis apparatus and kit of the present invention;

FIG. 4 is a diagram of the cathodic protection apparatus used in accordance with the present invention for underground storage tanks protected with an impressed system.

Figure 2:
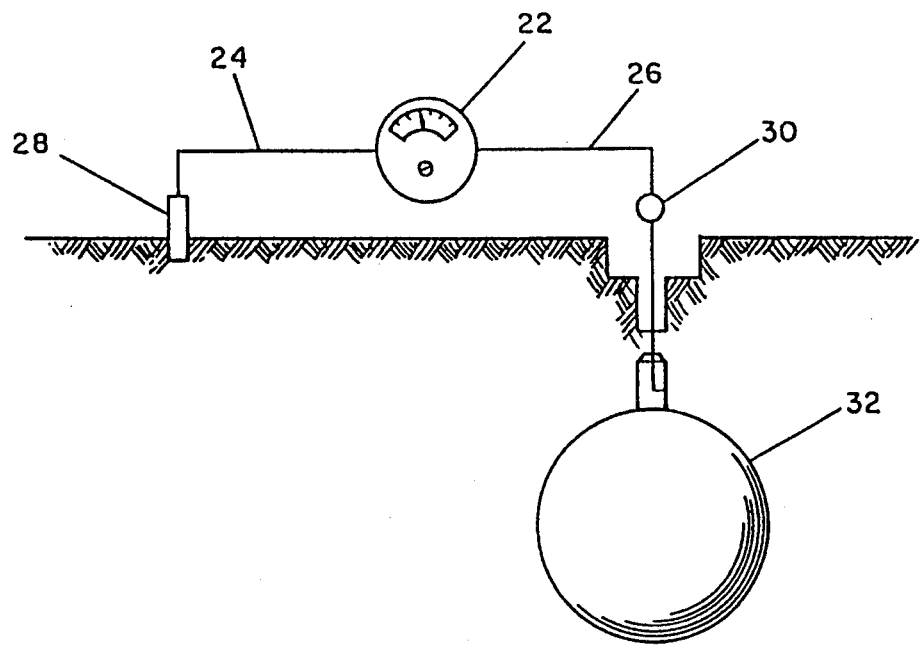
FIG. 2 is a diagram of the corrosion potential apparatus used in accordance with the present invention.

DESCRIPTION OF THE PREFERRED EMBODIMENTS (BEST MODES FOR CARRYING OUT THE INVENTION)

The present invention relates to methods and apparatuses/kits for detecting, in the field, leakage of hydrocarbons from underground storage tanks. The present invention also relates to the determination, in the field, of the presence of water in a tank and of the soil-to-tank potential, that is the potential of a metal underground storage tank to corrode, and for protecting the tank from corrosion or further corrosion, if warranted. More particularly, the present invention relates to methods and apparatuses/kits for analyzing on-site soil samples taken near an underground storage tank, for measuring the soil-to-tank potential of a metal tank, for detecting the presence of water within a tank, and for protecting a metal tank from corrosion or further corrosion by inducing current flow through the metal of the tank.

The methods and apparatuses/kits of the invention are referred to generally as "leakage detection," "corrosion potential," "water detection," and "cathodic protection." The invention relates to methods and apparatuses/kits separately and in various combinations. The terms "underground storage tank," "tank," and "underground tank," as used throughout the specification and claims, are intended to include any underground structure for the storage of petroleum products or hydrocarbons. Such terms may include, for example, what are commonly known in the art as underground storage tanks, both commercial and domestic, and also pipelines, buildings and other facilities, and the like, which are utilized for the storage of petroleum products and other hydrocarbons.

The preferred leakage detection method and apparatus/kit of the present invention comprise several components used in a particular manner. This invention is primarily intended for homeowners or small commercial users. First, a surface outline marking or staking the underground location of the tank is made. One or more holes are drilled in the soil near the underground tank and soil samples extracted. Some soil is set aside for later laboratory analysis, if needed. A small amount of the soil sample is field tested in the apparatus/kit of the invention, as follows. The soil is mixed with an extraction solvent, preferably hexane, the mixture is filtered, and the fluid evaporated. An oily smell or any residue remaining after evaporation of the fluid indicates that hydrocarbon leakage from the underground storage tank may have occurred, and the retained soil sample and the residue may be sent to a laboratory, at a later time, for a more detailed analysis. Hexane is the solvent of choice for detecting hydrocarbons heavier than gasoline, such as home heating oil, waste oil, and diesel fuel.

The leakage detection kit may also be used to determine the efficiency of cleanup efforts after a hydrocarbon spill or leak. For example, soil contaminated by diesel fuel may have been excavated by a cleanup team. The team can use the kit in the area of excavation or outside to determine whether additional excavation is needed to remove all spilled diesel fuel.

In the preferred embodiment, the leakage detection apparatus/kit of the invention, shown in FIGS. 1a–1c, comprises a vial or bottle filled with a solvent 12, such as hexane, filter paper 14, and canister or evaporating dish 16. This apparatus and kit is used for testing the soil surrounding an underground storage tank for evidence of leakage of hydrocarbons. First, a surface outline showing the underground location of the tank, if not obvious, is marked or staked on the surface above the underground storage tank. Holes (e.g., two holes each two inches in diameter) are drilled in the soil, for instance, one on either side of the tank. The holes are drilled preferably from three to five feet from the edge of the tank and drilled to the level of the bottom of the tank, usually five to seven feet deep for standard underground storage tanks.

Soil is extracted from each drilled hole, using care (e.g., utilizing plastic gloves) not to contaminate the sample. Surface soil may be contaminated from aboveground spills, rather than leakage from the underground storage tank, so the surface soil should not be included in the sampling. Soil from each hole (e.g., one and one-half inch in depth) may be placed in a separate retention container, made of a metal, glass, plastic or other material which will not react with or contaminate the soil sample, for later lab analysis if the on-site test shows positive for hydrocarbons. Soil from each hole (e.g., one-half inch in depth) is placed in a bottle or vial 10 containing solvent 12 (e.g., two ounces). The volume of extraction solvent to volume of soil should be approximately one to two (a higher ratio of solvent to soil is acceptable, but will increase evaporation time). Vial 10 is also made of a material which will not react with or contaminate the soil sample, such as glass, plastic, metal, and the like. Vial 10 is shaken for approximately three to five minutes or for a sufficient time, depending on the solvent 12, so that solvent 12 sufficiently reacts with any hydrocarbons which might be present in the soil. The preferred solvent used for extraction of hydrocarbons in the soil is hexane, which works well for detection of home heating oil, waste oil, and diesel fuel. Other solvents, such as benzene, toluene, and chlorofluorocarbons, or any other hydrocarbon solvent which evaporates in a short period suitable for a field test, may also be used in accordance with the invention; however, chlorofluorocarbons are known to cause depletion of the ozone layer and benzene and toluene are suspected carcinogens, and thus are not favored extraction solvents for the on-site or field testing of the invention.

The solvent/soil mixture is then filtered through preferably 10–20 micron porosity filter paper 14 (generally taking 15 to 20 minutes) so that the resulting fluid from the mixture drains into a canister or evaporating dish 16. Evaporating dish 16 is preferably made of metal or other material which will not react with or contaminate the soil/solvent mixture. Evaporating dish 16 preferably comprises a lid or cover 18 for storage and description of the soil sample. Cover 18 preferably comprises a label 20 for easily writing information about the soil sample, location, company name, address and telephone number, testing personnel, date, and the like.

Once fluid evaporates from evaporating dish 16, the soil tests positive for hydrocarbons if either any residue in dish 16 exudes an oily smell or feels oily, or any color remains. If no hydrocarbons are detected in the soil sample, then metal underground storage tanks are good candidates for the installation of cathodic protection, discussed below. Such cathodic protection will prevent corrosion or further corrosion of the metal underground storage tank from occurring. A yellow, brown, or black residue generally indicates the presence of hydrocarbons in the soil sample. Residue may then be inspected in evaporating dish 16 or wiped from dish 16 for closer inspection, e.g., using an unused sheet of filter paper 14. The term "inspection," as used throughout the specification and claims, is intended to include inspection through sight, smell, and touch. In the event of a positive test, the retained soil and the residue from dish 16 may be sent to a laboratory for more extensive testing. If the laboratory also confirms that hydrocarbons are present in the soil sample and that the hydrocarbons leaked from the tank, the tank must be inspected and replaced or repaired.

The preferred corrosion potential method of the present invention comprises several components used in a particular manner. Corrosion potential measurements would normally not be performed by a homeowner or small commercial entity. Holes are drilled in the ground near a metal underground storage tank. The holes are filled with water and an electrode, such as a copper/copper sulfate electrode, is placed in each hole. A wire lead is connected from the negative node of a voltmeter to the underground tank. Another lead is connected from the positive node to one reference electrode. A reading is then taken from the meter and the process repeated for each of the other electrodes. Readings of −0.29 to −0.80 volts or lower indicate that the tank is not, or only slightly, corroded and can benefit from cathodic protection. Higher readings indicate moderate to severe corrosion and that the tank should be replaced.

In the preferred embodiment, the corrosion potential apparatus used in accordance with the present invention, shown in FIG. 2, comprises voltmeter 22, wire leads 24 and 26, and electrode 28, such as copper/copper sulfate halfcell electrode. This apparatus is used for testing a metal tank for the degree of corrosion. Tank contacting probe 30, preferably of highly conductive metal such as steel, copper, or aluminum, is placed in contact with underground storage tank 32. Wire lead 24 is connected from tank contacting probe 30 to the positive node of voltmeter 22. Wire lead 26 is connected from the negative node of voltmeter 22 to electrode 28, which has been placed in a hole, filled with water, in the soil. The hole may be, for example, approximately two inches in diameter, sixteen inches deep, and three to five feet from underground storage tank 32. More than a single hole may be drilled, permitting measurements on various sides of underground storage tank 32 and permitting a greater likelihood of detection of regional anomalies in the corrosion of tank 32. If voltmeter 22 reads approximately −0.29 volts or greater, underground storage tank 32 is likely to be at least significantly corroded and replacement of the tank should be considered.

The preferred water detection method of the present invention comprises the use of several components used in a particular manner. A dip stick is coated at one end of the stick, with a reagent which turns color in the presence of water. The dip stick is then inserted, coated end down, into the underground storage tank until the coated end strikes the bottom of the tank, and then immediately withdrawn. The length of reagent which has turned color indicates the depth of any water at the bottom of the tank. If the dipstick has turned color, inspection of the tank and removal of the water may be warranted.

The preferred cathodic protection method of the present invention comprises both passive and impressed methods, depending on the need of the particular metal tank to be protected. Both the passive and impressed methods comprise several components used in a particular manner. The passive method employs one or more "sacrificial anodes" buried in the soil near the underground tank to be protected. Sacrificial anodes are made of materials based on the Galvanic Series, anodic relative to the material of the underground storage tank, so that the anode "sacrifices" its electrons to the tank. For instance, the sacrificial anodes may comprise magnesium, zinc, or aluminum alloy materials, or a combination thereof. When connected to the underground tank with one or more insulated wires, the sacrificial anode induces current flow through the tank and the soil, causing the sacrificial anode to corrode rather than the storage tank, which is cathodic relative to the sacrificial anode. The impressed method operates similarly except that current is induced by a direct current generator, which provides greater protection for the tank, albeit at an increased cost vis-a-vis a sacrificial system. Sacrificial anodes would be preferable for homeowners and small commercial entities.

Figure 3:
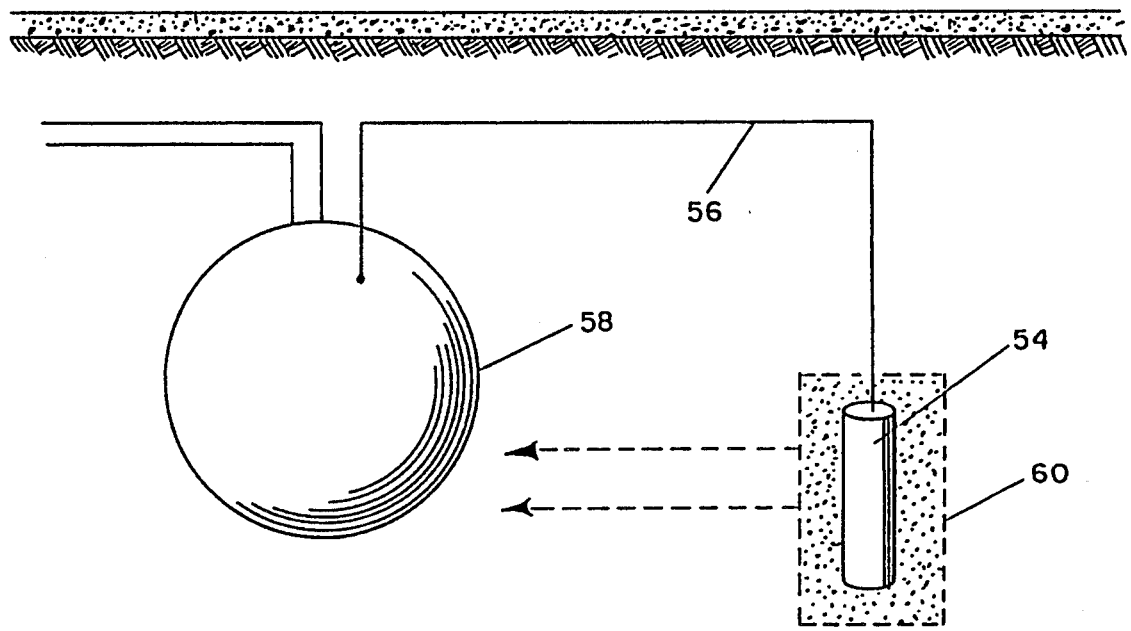
FIG. 3 is a diagram of the cathodic protection apparatus used in accordance with the present invention for underground storage tanks protected with a passive system.

In the preferred embodiment, the passive cathodic protection apparatus used in accordance with the present invention, shown in FIG. 3, comprises at least one sacrificial anode 54 and insulated wire 56. This apparatus is used to protect a metal underground storage tank 58 from corrosion by inducing current flow through tank 58 using sacrificial anode 54. Underground storage tank 58 is connected by insulated wire 56 to sacrificial anode 54. Sacrificial anode 54 may be surrounded by anode backfill 60, which comprises, for example, bentonite. Current flow is thereby automatically induced from sacrificial anode 54 through the surrounding soil, then through tank 58, and back to sacrificial anode 54 through insulated wire 56. Tank 58 is thereby made cathodic relative to sacrificial anode 54, which anode corrodes rather than tank 58.

In the preferred embodiment, the impressed cathodic protection apparatus used in accordance with the present invention, shown in FIG. 4, comprises a rectifier 62, insulated wire 64, and impressed current anode 66. This apparatus/kit is used to protect a metal underground storage tank 68 from corrosion by inducing current flow through tank 68 using an external power source. Underground storage tank 68 is connected by insulated wire 64 to the negative node of rectifier 62. The positive node of rectifier 62 is connected by insulated wire 64 to impressed current anode 66, and may be surrounded by anode backfill 70, which comprises, for example, bentonite. Impressed current anode 66 should also be made of a "sacrificial material" relative to the material of tank 68. When rectifier 62 is connected to an AC power source, current flow is thereby induced from impressed current anode 66 through the surrounding soil, then through tank 68, insulated wire 64, rectifier 62, and back to impressed current anode 66 through insulated wire 64. Tank 68 is thereby made cathodic or more cathodic relative to impressed current anode 66.

The methods and apparatuses of the present invention provide means by which the performance of underground storage tanks may be judged and, if the tank is metal and not extensively corroded, the tank protected. The present invention eliminates costly and time-consuming laboratory intervention in many cases, which makes it more likely that tanks will be checked for leakage, corrosion, and the presence of water on a regular basis.

Although the invention has been described with reference to these preferred embodiments, other embodiments can achieve the same results. Variations and modifications of the present invention will be obvious to those skilled in the art and it is intended to cover in the appended claims all such modifications and equivalents.

What is claimed is:

1. A kit for on-site or field analysis of soil for detecting the presence of hydrocarbons in the soil, the kit comprising:
   a container including; hexane as a solvent reactable with hydrocarbons in an amount sufficient to mix a desired soil sample therewith;
   sealable field container means for agitating a desired soil sample with said hexane to create a mixture of said hexane and the soil sample;
   filter paper for filtering soil solids from said mixture of the soil sample and said hexane; and
   an evaporating dish for evaporating said extraction fluid and inspecting any residue from said evaporation for detecting hydrocarbon presence from inspection of filtered extraction fluid.

2. The invention of claim 1 wherein said filter paper comprises size 20 micron or finer porosity.

3. The invention of claim 1, wherein said evaporating dish comprises a cover for storage of said residue.

4. The invention of claim 1 wherein said evaporating dish comprises label means for providing information on said evaporating dish.

5. A method for on-site or field testing soil for the presence of hydrocarbons, the method comprising the steps of:
   a) drilling at least one hole in the ground at a selected location;
   b) removing soil from the hole;
   c) placing the soil and hexane as a solvent reactable with hydrocarbons in a sealable field container;
   d) agitating the sealable field container thereby mixing the soil and the hexane;
   e) filtering solids from the mixture of soil and hexane;
   f) providing an evaporation dish;

g) evaporating, in said evaporating dish, the extraction fluid to produce a residue containing hydrocarbons, if present in the soil sample; and h) detecting the presence of hydrocarbons from inspection of filtered extraction fluid.

6. The invention of claim 5 wherein the step of detecting the presence of hydrocarbons comprises visually detecting a colored residue.

7. The invention of claim 6 wherein the step of detecting the presence of hydrocarbons comprises touching the residue tactually to feel the lubricating sensation caused by hydrocarbons.

8. The invention of claim 5 further comprising the step of drilling at least one hole from which to extract the soil at a selected location relative to an underground hydrocarbon storage tank.

9. The invention of claim 8 further comprising the step of drilling at least one hole down to a depth at least as deep as the bottom of the underground hydrocarbon storage tank.

* * * * *